(12) United States Patent
Chen et al.

(10) Patent No.: US 10,573,000 B2
(45) Date of Patent: Feb. 25, 2020

(54) SYSTEM AND METHOD FOR MEDICAL IMAGE MANAGEMENT

(71) Applicant: Beijing CuraCloud Technology Co., Ltd., Beijing (CN)

(72) Inventors: Hanbo Chen, Seattle, WA (US); Hao Chen, Beijing (CN); Youbing Yin, Kenmore, WA (US); Shanhui Sun, Princeton, NJ (US); Qi Song, Seattle, WA (US)

(73) Assignee: Beijing Curacloud Technology Co., Ltd., Beijing (CN)

( * ) Notice: Subject to any disclaimer, the term of this patent is extended or adjusted under 35 U.S.C. 154(b) by 0 days.

(21) Appl. No.: 16/128,483

(22) Filed: Sep. 11, 2018

(65) Prior Publication Data

US 2019/0228524 A1 Jul. 25, 2019

Related U.S. Application Data (60) Provisional application No. 62/620,689, filed on Jan. 23, 2018.

(51) Int. Cl.

| | |
|---|---|
| *G06K 9/00* | (2006.01) |
| *G06T 7/00* | (2017.01) |
| *G06K 9/62* | (2006.01) |
| *G06K 9/03* | (2006.01) |
| *G16H 30/00* | (2018.01) |

(52) U.S. Cl.
CPC .......... *G06T 7/0012* (2013.01); *G06K 9/033* (2013.01); *G06K 9/6227* (2013.01); *G06K 9/6242* (2013.01); *G06K 9/6257* (2013.01); *G06K 9/6259* (2013.01); *G06K 2209/05* (2013.01); *G06T 2207/20084* (2013.01); *G06T 2207/30004* (2013.01); *G16H 30/00* (2018.01)

(58) Field of Classification Search
None
See application file for complete search history.

(56) References Cited

U.S. PATENT DOCUMENTS

| | | | | |
|---|---|---|---|---|
| 2012/0113239 | A1* | 5/2012 | Krupnik | A61B 1/00009 348/65 |
| 2012/0316421 | A1* | 12/2012 | Kumar | A61B 1/00009 600/407 |
| 2017/0098329 | A1* | 4/2017 | Westerhoff | G06T 19/20 |
| 2018/0137244 | A1* | 5/2018 | Sorenson | G06F 19/321 |
| 2018/0341752 | A1* | 11/2018 | Bernard | G06F 19/345 |

* cited by examiner

*Primary Examiner* — Wei Wen Yang
(74) *Attorney, Agent, or Firm* — Bayes PLLC (57) ABSTRACT

The present disclosure is directed to a method and device for managing medical data. The method may include receiving medical image data of a plurality of patient cases acquired by at least one image acquisition device. The method may further include determining diagnosis results, by a processor, of the medical image data using an artificial intelligence method. The method may also include determining, by the processor, priority scores for the medical image data based on the respective diagnosis results, and sorting, by the processor, the medical image data based on the priority score. The method may yet further include presenting a queue of the medical image data on a display according to the sorted order.

20 Claims, 3 Drawing Sheets

SYSTEM AND METHOD FOR MEDICAL IMAGE MANAGEMENT

CROSS-REFERENCE TO RELATED APPLICATION

This application claims the benefit of priority to U.S. Provisional Application No. 62/620,689, filed on Jan. 23, 2018, the entire contents of which are incorporated herein by reference.

TECHNICAL FIELD

The present disclosure generally relates to medical imaging, and more particularly to medical image management.

BACKGROUND

Medical images play an indispensable role in clinical diagnosis. Most of the images, after being acquired, need to be examined and labeled by a radiologist. The radiologist then provides a pathological report to physicians. Due to the high volume of images that need to be examined, most hospitals or Internet-based remote diagnosis platforms use queuing systems to help manage the images. Radiologists may select medial images for processing based on the order in which they appear in the queue).

In general, a traditional system may sort patient cases according to the acquisition time of their respective medical images. Sorting the patient cases in this manner enables the patients to be examined on a first come first serve basis. Alternatively, a system may comprehensively consider the data acquisition time, the urgency of a disease and the workload of doctors to reasonably schedule and distribute the medical related data. For example, cerebral hemorrhage and cerebral thrombosis are two common acute diseases. Although both are cerebral blood diseases, the treatment methods of the two diseases are completely different. If the doctor can make a correct diagnosis within hours of illness and treat the patient accordingly, the risk of the diseases can be significantly reduced, and the rehabilitation of the patient can be improved. For such images, the queuing management system may assign a higher priority, place them at the top of the queue, and label the patient cases as emergency cases. If an emergency case that requires immediate processing enters into the queue, a radiology may rearrange non-emergency works at hand and handle the emergency case immediately.

It is noted that the priorities of the medical images are typically derived from the priority of the disease conditions of the patient cases. The priority of a disease condition is typically decided manually by a physician handling the case (e.g., he may determine the condition based on the symptoms of the patient). Such a determination is vulnerable to diagnosis errors (e.g., the physician may misdiagnose the seriousness of a patient's condition). Consequently, priorities of certain cases may be underestimated, and the optimal treatment time window may be delayed. Moreover, physicians often need to refer to examination results provided by radiologists in order to make informed decisions. Because medical images of certain cases may need to be sorted before examination results are made available, the sorting performed in such cases may not be meaningful. Furthermore, radiologists tasked to sort the medical images may be overloaded with other tasks, which may lead to additional human errors, further reducing the accuracy and efficiency of the image management system.

SUMMARY

In one aspect, the present disclosure is directed to a computer-implemented method for managing medical data. The method may include receiving medical image data of a plurality of patient cases acquired by at least one image acquisition device. The method may further include determining diagnosis results, by a processor, of the medical image data using an artificial intelligence method. The method may also include determining, by the processor, priority scores for the medical image data based on the respective diagnosis results, and sorting, by the processor, the medical image data based on the priority score. The method may yet further include presenting a queue of the medical image data on a display according to the sorted order.

In another aspect, the present disclosure is directed to a medical image management system communicatively connected with at least one image acquisition device. The system may include a communication interface configured to receive medical image data of a plurality of patient cases acquired by the at least one image acquisition device. The system may further include a processor, configure to determine diagnosis results of the medical image data using an artificial intelligence method, determine priority scores for the medical image data based on the respective diagnosis results, and sort the medical image data based on the priority score. The system may also include a display configured to present a queue of the medical image data according to the sorted order.

In yet another aspect, the present disclosure is directed to a non-transitory computer readable medium having instructions stored thereon. The instructions, when executed by a processor, perform a method for managing medical data. The method may include receiving medical image data of a plurality of patient cases acquired by at least one image acquisition device. The method may further include determining diagnosis results of the medical image data using an artificial intelligence method. The method may also include determining priority scores for the medical image data based on the respective diagnosis results, and sorting the medical image data based on the priority score. The method may yet further include presenting a queue of the medical image data on a display according to the sorted order.

It is to be understood that the foregoing general description and the following detailed description are exemplary and explanatory only, and are not restrictive of the invention, as claimed.

DETAILED DESCRIPTION

Reference will now be made in detail to the exemplary embodiments, examples of which are illustrated in the accompanying drawings. Wherever possible, the same reference numbers will be used throughout the drawings to refer to the same or like parts.

The term "medical image data" used throughout this disclosure includes, but is not limited to, the medical image data, and may also include other related data, for example, the attribute information (such as acquisition time, upload time, data source and the like) of the medial images, for example, the examination type to which the medical images belong, and the subject attribute information (such as the subject's age, height, weight, gender, medical history and the like). The term "sort," used throughout this disclosure, includes but not limited to prioritizing the medical image data such as arranging the sequence of the medical image data based on at least the priority score of the medical image data. For example, the medical image data with higher priority may be ranked higher in the sequence (queue).

Embodiments of the present disclosure provide a medical image management method. The method may be implemented by a computer. Specifically, after medical image data are acquired for each patient case, the method may further process and analyze the medical image data to obtain a priority score of the medical image data. Such analysis process can make a preliminary judgment by using artificial intelligence modules to evaluate the disease condition of the patient. The final sorting can be performed depending on the priority scores. The method can also take additional factors into consideration. Such factors may include, but are not limited to: the physician's judgment, the attribute information of the medical images including the data acquisition time, and the decision of the artificial intelligent module. Moreover, for non-emergency cases, the method can also consider comprehensively the workload of the doctors in the scheduling process.

Figure 1:
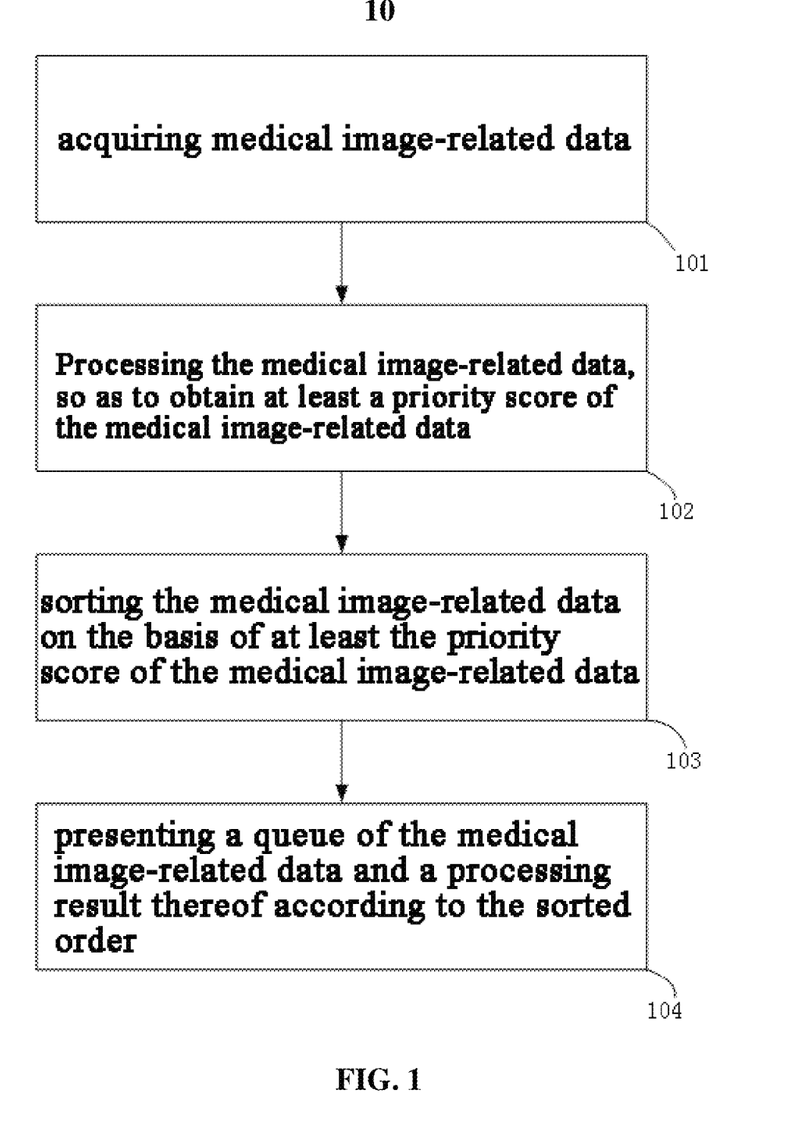
FIG. 1 is a schematic flow diagram of a medical image management method implemented by a computer, according to a disclosed embodiment.

FIG. 1 shows an embodiment of a medical image management method 10 configured in accordance with the present disclosure. Method 10 may include acquiring medical image data (Step 101); processing, by a processor, the medical image data, to obtain at least a priority score of the medical image data (Step 102); sorting, by the processor, the medical image data based on at least the priority score of the medical image data (Step 103); and presenting, by the processor, a queue of the medical image data and a processing result thereof according to the sorted order (Step 104).

The processor may be a processing device that includes one or more general processing devices, such as a microprocessor, a central processing unit (CPU), and a graphics processing unit (GPU), and the like. More specifically, the processor may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The processor may also be one or more dedicated processing devices such as application specific integrated circuits (ASICs), field programmable gate arrays (FPGAs), digital signal processors (DSPs), system-on-chip (SoCs), and the like.

The processor may be communicatively coupled to the storage and configured to execute computer-executable instructions stored therein, each of the steps mentioned above may be stored on the storage in the form of computer-executable instructions. The storage may include a read only memory (ROM), a flash memory, random access memory (RAM), a static memory, etc. In some embodiments, the storage may store computer-executable instructions of any one of Steps 101-104, and the data used or generated while executing computer-executable instructions, such as priority scores, a queue for the medical image data, and a processing result thereof.

The respective priority score may be used for evaluating the level of emergency of the patient case (e.g., the priority of the medical image data of the patient in the processing queue of the doctor). Utilizing method 10, medical image data can be processed by a processor automatically to obtain a priority score. Method 10 can also sort the medical image data in a queue accordingly and present the queue of medical image data in real time to the radiologist for processing. Method 10 can process newly acquired medical image data in real time. For example, method 10 can also sort all medical image data to be processed in nearly real time, and present the same to the radiologist.

Figure 2:
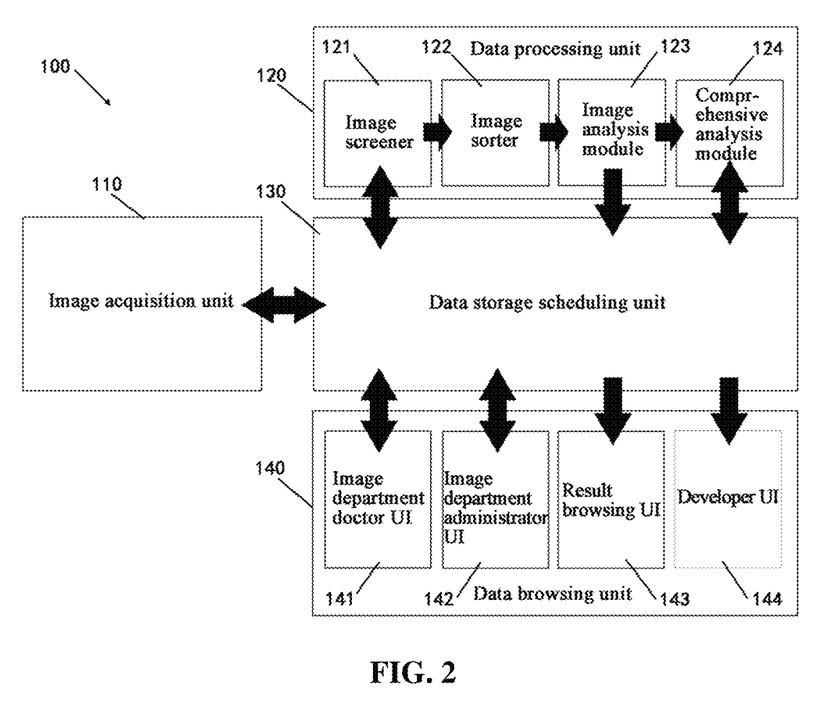
FIG. 2 is a block diagram of a medical image management system implemented by a computer, according to a disclosed embodiment.

FIG. 2 shows a block diagram of a medical image management system 100. System 100 may be implemented using a computer or a server. In some embodiments, system 100 may have different modules in a single device, such as an integrated circuit (IC) chip (implemented as an application-specific integrated circuit (ASIC) or a field-programmable gate array (FPGA)), or separate devices with dedicated functions. In some embodiments, one or more components of \system 100 may be located in a cloud, or may be alternatively in a single location (such as inside an imaging center) or distributed locations. Components of system 100 may be in an integrated device, or distributed at different locations but communicate with each other through a network (not shown).

As shown in FIG. 2, medical image management system 100 includes an image acquisition unit 110, which is used for acquiring medical image data and uploading the same to a data storage scheduling unit 130. Medical image management system 100 further includes a data storage scheduling unit 130, which is communicatively connected with the image acquisition unit 110 and a data processing unit 120, and used for transmitting, storing, sorting (based on the analysis result of the data processing unit 120), scheduling the data and recording the result. Medical image management system 100 also includes a data processing unit 120, which is configured to receive medical image data transmitted by the data storage scheduling unit 130, process and analyze the received medical image data, and feed the analysis result back to the data storage scheduling unit 130 for sorting and scheduling. Medical image management system 100 further includes a display unit 140, which is communicatively connected with the data storage scheduling unit 130, and displays to a potential user, e.g., a radiologist, an administrator, a developer and the like, various browsing interfaces with various display contents according to the sorted order and scheduling thereof. In some embodiments, the display contents include a queue presentation of the medical image data. It is noted that, the image acquisition unit 110 is not necessarily an internal unit of system 100. In some embodiments, image acquisition unit 110 may be an external system communicatively connected with system 100. System 100 obtains medical image data therefrom and uploads the same to the data storage scheduling unit 130.

In some embodiments, the data storage scheduling unit 130 is responsible for receiving, transmitting, storing, sorting and scheduling of the medical image data. Medical image data can be directly uploaded to the data storage scheduling unit 130 from the image acquisition unit 110, which is a local or remote imaging system. Image acquisition unit 110 may use various imaging modalities including, but not limited to, magnetic resonance imaging (MRI)

images, 3D MRI, 2D fluidized MRI, 4D volume MRI, computed tomography (CT) images, cone beam CT, positron emission tomography (PET) images, functional MRI images (such as fMRI, DCE-MRI and diffusion MRI), X-ray images, fluorescence images, ultrasound images, radiotherapy shot images, single photon emission computed tomography (SPECT) images, and so on). For example, the image acquisition unit 110 may be an MRI imaging device, a CT imaging device, a PET imaging device, an ultrasound device, a fluoroscopic device, a SPECT imaging device, or other medical imaging devices used for acquiring one or more medical images of a patient. Image acquisition unit 110 may also be a multi-modality imaging system using two or more of the imaging modalities. The acquired images may be stored in a database as imaging data and/or the medical image data. The data storage scheduling unit 130 may be communicatively connected to the database, to retrieve the medical image data stored therein. For example, the acquired images may also be stored in the storage included in the medical image management system 100, to be retrieved and used by the data storage scheduling unit 130.

In addition to the image acquisition unit 110, the data storage scheduling unit 130 may also acquire other medical image data from other units or systems. For example, it may obtain the type of examination to which the medical image acquisition is prescribed for, the age, height, weight, gender, medical history, and so on of the patient from a hospital information system (HIS) and/or an electronic medical record system.

A B/S (Browser/Server, namely a browser and a server framework, user working interface is implemented mainly through the browser) structure-based service may be designed to receive medical image data. A user only needs to login by using the user name and password, and then he/she can perform a data uploading operation. The service labels, upon the data uploading, each of the uploaded data, the label includes but is not limited to data acquisition time, uploading time, data source, and so on. After the labeling, the data enters a waiting queue, and is prepared to be sequentially fed by the data storage scheduling unit 130 into the data processing unit 120 for performing analysis and calculation to obtain an analysis result.

According to the analysis result fed back by the data processing unit 120, the data storage scheduling unit 130 carries out the corresponding data transmission and scheduling. For example, if the result of the feedback is that the image quality is unsatisfactory, the data storage scheduling unit 130 forwards the feedback result to an image acquisition unit 110. Otherwise, for data that is satisfactory, the data storage scheduling unit 130 receives an automatic diagnosis result from the data processing unit 120. According to the sorted order and scheduling rules, if there is a problem with the automatic diagnosis result, the data storage scheduling unit 130 transmits the data (that may include the automatic diagnosis result) to a first doctor and waits for the diagnosis result from the first doctor. After the diagnosis result from the first doctor is received, the automatic diagnosis result can be compared with that of the first doctor. If the comparison result is inconsistent, the data storage scheduling unit 130 forwards the result to another or more doctors for a comprehensive diagnosis to reduce the probability of misdiagnoses. It is noted that, the determination of whether the diagnosis result is false may be performed by a comprehensive analysis module 124 below in the data processing unit 120. The comprehensive analysis module 124 instructs the data storage scheduling unit 130 to perform the corresponding data transmission according to the determination result, for example, send the data (which may include the automatic diagnosis result) to the first doctor, and receive a diagnosis result from the first doctor. In addition, the comprehensive analysis module 124 can compare the automatic diagnosis result with the diagnosis result of the first doctor, and instruct the data storage scheduling unit 130 to perform the corresponding data transmission according to the comparison result, for example, send the data to another or more doctors for a comprehensive diagnosis, and then carry out a comprehensive analysis on the diagnosis results from the respective doctors, to obtain a final data processing result, including a diagnosis result, a priority score and the like.

The data storage scheduling unit 130 returns the final diagnosis result to the doctor who prescribed the imaging exam and/or the patient. In some embodiments, the data storage scheduling unit 130 records the wrong diagnosis results to provide reference for subsequent developments.

In some embodiments, when the automatic diagnosis result is inconsistent with the final diagnosis result, the data storage scheduling unit 130 transmits the final diagnosis result to the data processing unit 120, the data processing unit 120 may use the final diagnosis result data as training data to train an artificial intelligence analysis module therein for correction and improvement thereof, to improve the analysis precision of the artificial intelligence analysis module.

The medical image management system 100 may dynamically turn on/off computing nodes according to the number of patient cases (medical image data) in the queue, to save computational resources while ensuring computational efficiency. For example, when the number of cases waiting in the queue is above a certain threshold, the system 100 may turn on new nodes to improve computational efficiency. When no case needs to be processed, the system 100 may turn off idle nodes to save resources.

The data storage scheduling unit 130 may also perform queue management operation, by using a priority list for dynamically sorting the priorities of the medical image data. The sorting in the list is based on the priority score of the data. In general, the score may be set as a score within a fixed range (such as 0 to 100). The higher the score is, the higher the order is in the queue. The data that newly enter the list are transmitted through the data storage scheduling unit 130 to the data processing unit 120, and the data processing unit 120 calculates and returns a priority score of the medical image data. Medical image data may be directly sorted based on the priority score returned by the data processing unit 120 and obtained by the processor through image processing. Moreover, medical image data may also be sorted with the assistance of other priority scores obtained in other manners. For example, predetermined scoring rules may also be adapted for regenerating a processing priority score.

Table 1 provides a specific example of scoring rules (the total score that exceeds 100 is set as 100):

TABLE 1

An example of scoring rules

| Category | Item | Score |
| --- | --- | --- |
| Examination type | Emergency | 100 |
| | Etiological screening | 50 |
| | Routine physical examination | 0 |
| Bonus points | Brain image | +20 |
| | Cardiac image | +15 |

As shown in table 1, scores are different depending on whether the examination type is emergency, etiological screening, or routine physical examination; different bonus points correspond to different plus scores. Table 1 does not list the scoring rules in an exhaustive manner, and other factors may also be considered for the scoring rule. Out of the priority score obtained through image processing by the data processing unit 120 and the priority score obtained according to the artificially set rules, the higher one may be taken as a queuing score. It is noted that, the step of scoring according to the predetermined rules may not be necessarily performed in the data storage scheduling unit 130, and may also be performed in the data processing unit 120, and the higher score may be taken therein as a final priority score and transmitted to the data storage scheduling unit 130.

In the actual operation process, the medical image data, on which the data processing unit 120 cannot perform image processing, can be directly set to be scored by using a preset rule, to ensure that each of the medical image data can be properly and timely processed in the queue.

In the actual queue scheduling process, medical image data are inserted to the corresponding position in the list based on the priority score. In some embodiments, the priority score can increase over time after entering the queue. In this way, the scheduling process can ensure that the data will be set to a high priority when it stays in the queue for too long. The scheduling process can also reduce, to some extent, the extra risk caused to a patient due to a long treatment time. The scheduling process configured in this manner will make sure that all cases in the queue will be taken care of in time (e.g., a priority score will be increased and becomes high when the case stays in the queue for a long time even if its initial priority score is low). For certain instances, the increase made to the priority score can depend on an initial score of medical image data and a data processing rate specified by the hospital. Such a design can also ensure that all the data processing can be completed within a specified time limit. For example, if the specified time limit is 120 minutes, the initial priority score of the data is 40 points out of 100 points, and the time for processing the data is less than 10 minutes, then the score of the data can be increased by (100-40)/(120-10)/60=0.009 per second. In order to ensure that an emergency case is always at the top of the queue, the increase rate can be changed into a very small value when the score is close to 100 points, to ensure that the score of non-emergency cases cannot exceed 100 points. For example, when the score increases to 99 points, the increase rate is reduced to be 1e-5. However, for an emergency case, its initial score is 100 points, and the increase rate is also 1e-5. To maintain a very small increase rate is to ensure that the relative position of the data in the queue does not change.

The above queue adjustment based on the priority score enables medical image data of the patient with more urgent disease condition to be preferentially seen and processed by the doctor. In some embodiments, access to the queue of medical image data may be shared by a number of the doctors. For instance, for a small hospital or medical image processing department, a queue with complete medical image data can be set to be visible to all the doctors. This way, each doctor can select the data from the queue for processing. The system may be configured differently for a large hospital. For instance, the system can have separate queues for different individuals and distribute the queues of data to those individuals accordingly. The system may automatically distribute the data to different doctors, so that each doctor has a queue to his/her own and is responsible for processing the data in that queue. The data storage scheduling unit 130 is responsible for matching the data with the doctors, to transmit the specific data to the most appropriate radiologist for subsequent processing.

The following steps can be performed for matching the data with the doctors. In some embodiments, medical image data may be distributed according to the current work schedule of the doctors. For example, the data associated with an emergency patient case (e.g., having a relatively higher priority score) can be distributed to the doctor having the minimum emergency cases at hand. As another example, ordinary data can be distributed to the doctor best able to process such cases. If a doctor suitable to process such data is too busy, then the data can be distributed to a less busy doctor. In some embodiments, the data storage scheduling unit 130 can also monitor the processing status of the data. When the specified time limit of the data is approaching, but the doctor to whom the data are distributed has not yet processed the data, the data storage scheduling unit 130 can remind the doctor in a visual form such as highlight. In some embodiments, the data storage scheduling unit 130 can present the status of the patient case where the processing time limit for which is approaching but not yet processed by a doctor, on the interface of the image department administrator. In some embodiments, the data storage scheduling unit 130 can automatically distribute the task to another radiologist with the current priority, to ensure that the processing result may be obtained on time.

Medical image data are transmitted to the data processing unit 120 through the data storage scheduling unit 130. In the data processing unit 120, the medical image data are processed by a processor, to obtain at least a priority score of the medical image data. The data processing unit 120 may include an image analysis module 123, which is used for processing the medical image data, to obtain at least a priority score of the medical image data.

In some embodiments, as shown in FIG. 2, the data processing unit 120 can include an image screener 121, to perform screening for the medical image data before processing, to ensure that different categories of data can be respectively processed both appropriately and efficiently. The data processing unit 120 can also avoid wasting computational resources and time on the data which is not satisfactory. In some embodiments, the data processing unit 120 may include an image sorter 122, which is used for classifying medical image data according to the modalities and imaging sites. Accordingly, a suitable image analyzer in an image analysis module 123 is selected for data processing, to obtain at least a priority score of the medical image data. In some embodiments, the data processing unit 120 may also include a comprehensive analysis module 124 for a comprehensive analysis of the processing result of the image analysis module 123 and other information, to obtain a more reliable final priority score and reduce the probability of misdiagnoses. It is contemplated that the data processing unit 120 may include more or less components than what are shown in FIG. 2. Data processing unit 120 may also include components different from the image screener 121, the image sorter 122, the image analysis module 123 and the comprehensive analysis module 124 shown in FIG. 2.

In some embodiments, the acquired medical image data is screened through an image screener 121, and data that passes the screener 121 can then be processed by the processor (such as the image sorter 122, the image analysis module 123 and the comprehensive analysis module 124).

In some embodiments, the acquired medical image data are screened through the image screener 121, and divided into several classes: invalid data, processable data, unqualified data, and unknown data. The invalid data refer to the data without image or incomplete data. The unqualified data refer to the low-quality data such as data with a low signal-to-noise ratio. For these classes of data, the data processing unit 120 will inform the user immediately, so that the user can take another imaging examination immediately to provide updated image data. If no update data is returned by the image acquisition unit within a short time period, the data as is will be put into the list according to predetermined rules for the radiologist to confirm and process.

Unknown data refer to data of a type that has never appeared in the training data set of the classifier (for example, which may be used for the image sorter 122, and may also be used for the image analysis module 123) in the data processing unit 120. For example, if the training data set for the classifier only included CT images of human bodies, then for this classifier, images of other modalities or medical images of animals will be classified as unknown data. Unknown data can be put into the to-be-processed data list according to the predetermined rules, waiting for the radiologist to process. At the same time, the data can also be recorded to provide reference for subsequent developments, such as to train a new classifier. The data can be directly transmitted to a subsequent data automatic processing unit, such as the image sorter 122, the image analysis module 123 and the comprehensive analysis module 124, for subsequent processing. Processable data are data ready to be added to the data list for the radiologist to process.

The image screener 121 can be implemented based on a variety of different algorithms. For example, a noisy image can be excluded through calculating the signal-to-noise ratio of the image by comparing an original image and a smoothed image. In another example, a noisy image without valuable information (such as a blank image) can be identified by calculating the entropy values of the (smoothed) image. Such an image can be excluded from processing. In yet another example, image data can be screened by a classifier. In some embodiments, the classifier can be trained by applying one-class support vector machine to the training data set. The one-class support vector machine is an unsupervised support vector machine algorithm. The algorithm can learn from the training data, and obtain the features distribution interval of the data through calculation. In some embodiments, data screened by image screener 121 may be labeled as sortable.

In some embodiments, the data labeled by the image screener 121 as sortable will be transmitted to image sorter 122 for automatic sorting. The image sorter 122 may be configured as a module for implementing the classification of the modalities and imaging organs for the medical image data according to the image features. Due to different modalities and different imaging sites, the image data are inherently different, and the image analyzer suitable for a certain modality (such as CT) and a certain imaging site (such as mammary gland) is not necessarily suitable for the image analysis of other modalities (such as MR) and other imaging sites (such as brain). To solve this problem, in some embodiments, multiple image analyzers can be provided corresponding to the modalities and the imaging sites of the medical images respectively. In some embodiments, the most suitable image analyzer may be identified based on nature and characteristics of the image data.

In some embodiments, the image sorter 122 may determine the modality of the image and the imaging organ based on the image features. The image sorter 122 may also divide the image into different sub-images according to organ sites and forward the sub-images to different image analyzers for processing. For example, the chest CT image usually contains 3D images of different organs, such as lung, spine, rib, cardiac and the like. In some embodiments, image patches of different organs can be obtained by performing segmentation on the original image. Such images may then be delivered to the corresponding different image analyzers for a targeted analysis.

The image sorter 122 may be implemented by different computer programs, including but not limited to an image retrieval program, an image classification program, and so on. For example, the image sorter 122 may be specifically implemented by the image retrieval algorithm. The basic process of the algorithm is as follows: generating a set of feature values for each of sample images and the images to be processed, and finding the closest sample image by matching the feature values of the image to be processed with that of the sample images, to achieve the purpose of classification. Further, the image features be extracted using, e.g., a Histogram of Oriented Gradient (HOG) feature algorithm, a Local Binary Pattern (LBP) feature algorithm, and Haar feature algorithm, or a multi-layer convolution-based deep convolution network. In some embodiments, the deep convolution network can be trained either by a supervised classification method or by an unsupervised automatic coder. In some embodiments, in order to effectively reduce the feature dimension to improve the matching efficiency, a feature cooling algorithm may be used. The algorithms may include a principal component analysis (PCA) method, an independent component analysis (ICA) method, a dictionary learning and sparse coding algorithm, and the like, and the more advanced machine learning algorithms include bag-of-words model, word vector model (such the word2vec tool) and the like.

Alternatively, the image sorter may also be implemented as a part of the image classification algorithms. For example, a deep convolution network may be trained to classify the image into different organs and different modalities. The input of the deep convolution network is an original image, and the output is a probability that the image belongs to each specified type. The deep convolution network first extracts the image feature information by combining a plurality of convolution layers, and then calculates a final probability value through a plurality of fully connected layers. The convolution kernel and the connection weight in the network are obtained through computer optimization. The deep convolution network can also predict the existence of multiple targets at the same time in one image and find the corresponding sub-regions. Different sub-images can be generated for each sub-region, so that the original image can be further sorted. It is noted that, the deep convolution network can also be implemented as a fully convolutional network, and the computation is accelerated by utilizing the high-speed computing characteristics of convolution.

In some embodiments, the image analysis module 123 may include a plurality of image analyzers. Each image analyzer is designed to perform calculation with respect to a specific modality and a specific organ. The image analyzer may be a deep learning (e.g., neural network) based algorithm, or other artificial intelligence algorithms. For example, the image analyzer may implement one or more algorithms of deep neural network, Random Forest, and Gradient boosting decision tree. The processing result of the image analyzer on the medical image data includes a diagnosis result, a related region and a priority score of the medical image. The diagnosis result refers to a related pathological analysis and the measurement of physiological index obtained based on the image. For example, the diagnosis result may be the probability of a certain disease feature represented by the image features, and may also be the size, volume, morphological analysis and tissue structure analysis of a specific organ. The related region refers to a region of interest. The related region may be labeled by one or more images. Each pixel in the image may be a number indicative of a certain region the pixel belongs to, or a probability that the pixel belongs to the region. The related region may also be a region surrounded by one or more computer graphics (such as straight lines, curves, squares, and circles). The priority score reflects the temporal emergency of the disease condition of the subject. For a patient in emergency (such as cerebral hemorrhage) who needs to be treated immediately, the image analyzer can generate a high priority score, and a relatively low priority score is given to the image without obvious disease symptoms.

For example, the diagnosis result may be obtained based on the processing results by using an image classification algorithm similar to that used by the image screener 121. For example, the related region in the processing result may be obtained by an image segmentation algorithm. For example, the image segmentation algorithm may be used to detect a lesion (focus) and segment the related area. In some embodiments, the algorithm may be deep a learning algorithm using a fully-convolution network. The input of the algorithm is an original image, and the output is a probability map of the segmented object. Multiple convolution layers may be used, to extract the related image features, based on which a final judgment can be made. The algorithm can be used for segmenting any anatomical structure of the object, such as a lesion area, or an organ in the image. For example, when the classification is performed using a deep convolution network, a network backward algorithm can also be used to retrieve the decision-making region in the image, to locate a potential lesion area. The network backward algorithm may determine a gradient-descent value used for network parameter optimization reversely act as a variable value transmitted in the network, to estimate an area (such as a potential lesion area) that plays a positive influence on a certain decision.

As an example, the priority score in the processing result may be obtained based on the diagnosis condition (such as the above-mentioned diagnosis result obtained by the image analyzer, or diagnosis classification as shown in table 1) of the medical images according to the pre-determined rules. In some embodiments, the image may be assigned a high priority score based on the associated diagnosis condition (e.g., a diagnosis result that the probability of cerebral vascular obstruction is over 80%), or an upcoming emergency examination of the image. Alternatively, the priority score can also be calculated directly from the image features with a regression algorithm. The regression algorithm can use an algorithm based on the deep convolution network, namely the original training output is replaced with the priority score. An algorithm such as a linear regression tree may also be used. For example, a priority score may be determined based on image features obtained by a convolution operation. Compared to using pre-determined rules, the linear regression algorithm is more flexible.

The scale of the priority scores may be specified by the doctor, for example, the priority of an emergency case (which needs to be treated immediately after admission) may be set at 100 points. For a patient whose examination result is healthy and has no disease, the priority may be set as 0 point. For a patient with chronic diseases, the severity of the disease condition may be determined according to with/without surgical operation, the medication situation, and the rehabilitation effect, and the priority score is determined accordingly.

In some embodiments, the analysis result of the image analysis module 123 may be further analyzed comprehensively, which may be implemented by the comprehensive analysis module 124. In some embodiments, a comprehensive analysis with respect to the diagnosis result of medical image data, the image features of the medial images, and the attribute information of a patient of the medical images may be performed. If there are different data for the same patient, the comprehensive analysis module will aggregate the different data for a final diagnosis. For example, if the same patient has medical image data of different modalities taken at different imaging sites, the processing results of these data can be aggregated for a final diagnosis. For example, if an ultrasonic image displays that a divergent and active blood flow exists at a certain site while a CT image displays that a heterogeneous structure exists at the same site, the two results can be aggregated to obtain a comprehensive diagnosis: a tumor exist with a large probability at that position. In another example, if multiple heterogeneous structures with active blood flow exist in the CT images and the ultrasonic images of other organs of the same patient, then a comprehensive diagnosis of tumor metastasis can be obtained, and accordingly, a higher priority score may be assigned.

The comprehensive analysis module 124 may also synthesize other information to reduce the possibility of misdiagnoses. For example, the image analyzer judges that the patient has the risk of senile dementia by processing the brain MRI image, but if the patient is found to be only 18 years old according to the case information, then the diagnosis result is not reliable and needs to be further corrected. The case information may come from medical image data.

In some embodiments, the comprehensive analysis module 124 may perform a comprehensive analysis on the respective priority scores of the same medical image data obtained in different ways. For example, the priority scores may be calculated with respect to the image features through various artificial intelligent algorithms, determined with respect to the attribute information of the medial images according to the artificially specified rules, artificially diagnosed and made by different doctors, and determined based on the diagnosis result of the medical images according to a preset rule, and so on. The comprehensive analysis may include one or more of discarding the deviation value, taking the highest value, taking the average value and the like.

The above-mentioned diagnosis results based on the medical images may synthesize other information through algorithms such as Bayesian Network, hidden Markov model, random forest algorithm, to obtain a final probability value for the disease. These algorithms will put the image-based diagnosis result, the image features used for calculating the diagnosis result, and other non-image information (such as age, height, weight, gender and so on) together as a feature value to be inputted for calculating. Output is a diagnosis result or a probability value that the patient suffers from disease(s). The Bayesian Network and the hidden Markov model work by the following steps: calculating a corresponding probability model through training data, to obtain a final probability value (output) accordingly. The random forest algorithm generates a final judgment result by performing random sampling on the feature values and samples to generate a plurality of decision trees for voting.

In some embodiments, the priority score is used for a dynamically adjusting the queue. When specifically implemented, an artificial intelligence-based means may be used for processing medical image data, to obtain a priority score, a diagnosis result, a related region and the like of medical image data. However, a correction mechanism may also be introduced if necessary. For example, if the comprehensive analysis module 124 finds there is a problem with the diagnosis result upon the comprehensive analysis, the obtained diagnosis result can be corrected by using various means. In some embodiments, the correction process may include: sending the medical image data to a first doctor and obtaining a diagnosis result of the first doctor; comparing the diagnosis result obtained by the image analysis module 123 with the diagnosis result of the first doctor; and obtaining a diagnosis result, a related region and a priority score of the medical image data based on the comparison result. The step of obtaining a diagnosis result, a related region and a priority score of the medical image data may further include: when the comparison result is inconsistent, sending both the diagnosis results to another doctor; and obtaining a diagnosis result, a related region and a priority score of the medical image data based on a comprehensive diagnosis result of the doctors.

Figure 3:
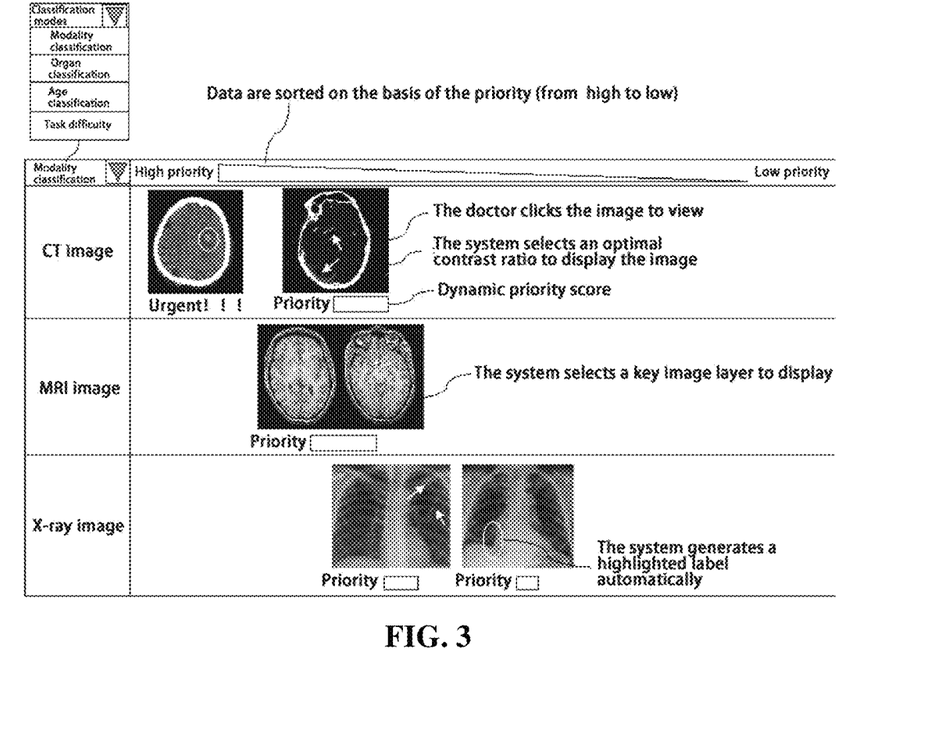
FIG. 3 shows a user interface for presenting medical image data to a radiologist in an order sorted based on priority, according to a disclosed embodiment.

According to the sorted order completed by the data storage scheduling unit 130, the queue of medical image data and the processing result thereof are presented on the data browsing unit 140. As shown in FIG. 3, the data browsing unit 140 may provide a plurality of user interfaces (UIs), to provide different users with the corresponding displays.

In some embodiments, a series of sorted patient image thumbnails will be displayed in the radiologist UI 141. FIG. 3 shows a radiologist UI 141. As shown in FIG. 3, the radiologist can display the to-be processed cases in categories by using various categorizing modes, including but not limited to modality classification, organ classification, age classification, task difficulty and the like. Each radiologist has different preferences. Some may specialize in diagnosis of a certain site or organ such as lung, and thus intend to categorize the to-be-processed cases by organ. Some may have preferences on a certain imaging modality. For example, when a radiologist who is not specialized in CT image processing finds that many urgent CT images have been assigned to him/her, he/she may provide feedback or submit the tasks to a supervisor through the UI 141 for reassignment, to more efficiently use the available human resource.

For example, if modality classification is selected, as shown in FIG. 3, the cases to be processed are classified as CT image, MRI image, X-ray image and other modalities and displayed accordingly. In each modality, medical image data are sorted from left to right based on the priority score from high to low. For example, in the CT image column, "Urgent" cases are arranged on the leftmost side, and the cases with relatively high priorities are arranged on the right side thereof, a dynamic priority score is displayed below each medical image. In some embodiments, a bar is displayed adjacent to the priority item, and the length of the bar represents the magnitude of the priority score, so that the radiologist can grasp the priority condition of the to-be-processed cases more intuitively. In some embodiments, the radiologist can click on the thumbnail to open the corresponding case for diagnosis. The thumbnail is generated by the data processing unit 120 according to the to-be-diagnosed medical images of the patient, for example, the data processing unit 120 may select an optimal contrast ratio, a key image layer and the like for displaying the medical images. In some embodiments, the data processing unit 120 may adjust the image brightness and select the displayed region according to the calculation result, and if a certain disease symptom is detected, then the related region will be highlighted. As shown in the X-ray image column in FIG. 3, the related region in the lung is labeled by the data processing unit 120 as being highlighted, to provide diagnosis assistance for the radiologist. In some embodiments, when the mouse hovers over a certain image, the image can be dynamically displayed. Automatic switching among different disease symptom images and the corresponding displaying may be also carried out. In some embodiments, the radiologist may select the calculation result of the data processing system to display, to reduce the range, improve working efficiency, and reduce the misdiagnoses rate. If a doctor encounters difficulty when processing the data, the doctor may submit the data to a higher-level doctor for processing through the UI 141. Then the data will enter a to-be-processed data queue of the higher-level doctor with the current priority score.

The image department administrator UI 142 enables a department administrator to supervise and schedule the data progress through the UI. The administrator can view the to-be-processed data, the processed data, and the statistics thereof of each radiologist through this UI. The administrator may recall the processed data for sampling inspection, and may also perform artificial adjustment and distribution among the data to be processed by different doctors.

The result browsing UI 143 may allow a non-radiologist to view a diagnosis result. At the same time, to the extent permitted by the hospital rules, the patient may also view, through the result browsing UI, for example, on his mobile terminal, his own image data, data processing progress, and data processing result report conveniently.

In some embodiments, a developer may view the wrong diagnosis result statistics of the artificial intelligence module through a developer UI 144, to correct error for the system and provide reference for subsequent system upgrade. Moreover, in some embodiments a computer readable storage medium may be provided. The computer-readable storage medium may store computer executable instructions thereon, wherein when executed by a processor, the processor may perform any one of the above methods. For instance, the processor may perform method including: acquiring medical image data; processing, by a processor, the medical image data, to obtain at least a priority score of the medical image data; sorting, by the processor, the medical image data based on at least the priority score of the medical image data; and presenting, by the processor, the queue of the medical image data and a processing result thereof according to the sorted order.

It is contemplated that the system disclosed herein may include one or more processor(s) and one or more storage device(s). It is contemplated that the processor(s) and the storage device(s) may be configured in a centralized or a distributed manner. The system may also include a medical database, an input/output device, a network interface, a display, and the like.

The processor may be a processing device that includes one or more general processing devices, such as a microprocessor, a central processing unit (CPU), a graphics processing unit (GPU), and the like. More specifically, the processor may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The processor may also be one or more dedicated processing devices such as application specific integrated circuits (ASICs), field programmable gate arrays (FPGAs), digital signal processors (DSPs), system-on-chip (SoCs), and the like.

The processor may be communicatively coupled to the storage device and configured to execute computer-executable instructions stored therein. The storage device may include a read only memory (ROM), a flash memory, random access memory (RAM), a static memory, a volatile or non-volatile, magnetic, semiconductor, tape, optical, removable, nonremovable, or other type of storage device or tangible (e.g., non-transitory) computer readable medium. In some embodiments, the storage device may store computer-executable instructions of one or more processing programs and data generated when a computer program is executed. The processor may execute the processing program to implement each step of the methods described above. The processor may also send/receive medical data to/from the storage device.

The system may also include one or more digital and/or analog communication (input/output) devices. For example, the input/output device may include a keyboard and a mouse that allow the user to provide input. The system may further include a network interface such as a network adapter, a cable connector, a serial connector, a USB connector, a parallel connector, a high speed data transmission adapter such as optical fiber, USB 3.0, lightning, a wireless network adapter such as a WiFi adapter, or a telecommunication (3G, 4G/LTE, etc.) adapter and the like. The system may be connected to the network through the network interface. The system may further include a display. In some embodiments, the display may be any display device suitable for displaying a medical image and its segmentation results. For example, the image display may be an LCD, a CRT, or an LED display.

The image being processed in this disclosure can be acquired by any type of imaging modalities, such as CT, magnetic resonance imaging (MRI), functional MRI (e.g., fMRI, DCE-MRI, and diffusion MRI), cone beam computed tomography (CBCT), Spiral CT, positron emission tomography (PET), single-photon emission computed tomography (SPECT), X-ray, optical tomography, fluorescence imaging, ultrasound imaging, and radiotherapy portal imaging, etc.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed system and related methods. Other embodiments will be apparent to those skilled in the art from consideration of the specification and practice of the disclosed system and related methods.

It is intended that the specification and examples be considered as exemplary only, with a true scope being indicated by the following claims and their equivalents.

What is claimed is:

1. A computer-implemented method for managing medical images, comprising:
   receiving medical image data of a plurality of patient cases acquired by at least one image acquisition device;
   determining diagnosis results, by a processor, of the medical image data using an artificial intelligence method;
   determining, by the processor, priority scores for the medical image data based on the respective diagnosis results;
   sorting, by the processor, the medical image data based on the priority scores;
   presenting a queue of the medical image data on a display according to the sorted order; and
   increasing the priority score of the medical image data at a first rate, as a time length since the medical image data enters the queue increases,
   wherein the first rate is reduced to a second rate when the priority score reaches a threshold.

2. The computer-implemented method of claim 1, further including:
   determining an imaging modality and an imaging site used to acquire the medical image data of each patient case, based on image features extracted from the medical image data; and
   selecting, based on the imaging modality and the imaging site, a corresponding image analyzer for analyzing the medical image data of the patient case, to obtain the diagnostic result.

3. The computer-implemented method of claim 1, wherein the artificial intelligence method includes at least one algorithm of deep neural network, random forest and gradient boosting decision tree.

4. The computer-implemented method of claim 1, wherein the patient cases are non-emergency cases, and wherein the priority score of the non-emergency cases does not exceed a priority score of an emergency case.

5. The computer-implemented method of claim 1, wherein the first rate is based on an initial priority score of the medical image data and a specified processing time for processing the medical image data in the queue.

6. The computer-implemented method of claim 1, wherein the priority score of the medical image data is determined by using a regression algorithm based on image features extracted from the medical image data.

7. The computer-implemented method of claim 1, further comprising:
   correcting the diagnosis result of medical image data of a patient case when the diagnosis result is inconsistent with a manually determined diagnosis result.

8. The computer-implemented method of claim 7, wherein correcting the diagnosis result further comprising:
   obtaining a first diagnostic result from a first doctor diagnosing the medical image data of the patient case;
   when the first diagnosis result is inconsistent with the diagnosis result, obtaining a second diagnostic result from a second doctor diagnosing the medical image data of the patient case;
   aggregating the first diagnosis result and the second diagnosis result to obtain a comprehensive diagnosis result; and
   correcting the diagnosis result based on the comprehensive diagnosis result.

9. The computer-implemented method of claim 1, further comprising:

identifying a plurality sets of medical image data associated with a same patient; and performing a comprehensive analysis of the plurality sets of medical image data to determine a comprehensive diagnosis result associated with the patient.

10. A medical image management system communicatively connected with at least one image acquisition device, the system comprising:
　a communication interface configured to receive medical image data of a plurality of patient cases acquired by the at least one image acquisition device;
　a processor, configure to:
　　determine diagnosis results of the medical image data using an artificial intelligence method;
　　determine priority scores for the medical image data based on the respective diagnosis results;
　　sort the medical image data based on the priority scores; and
　a display configured to present a queue of the medical image data according to the sorted order,
　wherein the processor is further configured to increase the priority score of the medical image data at a first rate, as a time length since the medical image data enters the queue increases, wherein the first rate is reduced to a second rate when the priority score reaches a threshold.

11. The medical image management system of claim 10, wherein the processor is further configured to:
　determine an imaging modality and an imaging site used to acquire the medical image data of each patient case, based on image features extracted from the medical image data; and
　select, based on the imaging modality and the imaging site, a corresponding image analyzer for analyzing the medical image data of the patient case, to obtain the diagnostic result.

12. The medical image management system of claim 10, wherein the artificial intelligence method includes at least one algorithm of deep neural network, random forest and gradient boosting decision tree.

13. The medical image management system of claim 10, wherein the patient cases are non-emergency cases, and wherein the priority score of the non-emergency cases does not exceed a priority score of an emergency case.

14. The medical image management system of claim 11, wherein the first rate is based on an initial priority score of the medical image data and a specified processing time for processing the medical image data in the queue.

15. The medical image management system of claim 10, wherein the priority score of the medical image data is determined by using a regression algorithm based on image features extracted from the medical image data.

16. The medical image management system of claim 10, wherein the processor is further configured to:

obtain a first diagnostic result from a first doctor diagnosing the medical image data of the patient case;
　when the first diagnosis result is inconsistent with the diagnosis result, obtain a second diagnostic result from a second doctor diagnosing the medical image data of the patient case;
　aggregate the first diagnosis result and the second diagnosis result to obtain a comprehensive diagnosis result; and
　correct the diagnosis result based on the comprehensive diagnosis result.

17. The medical image management system of claim 10, wherein the processor is further configured to:
　identify a plurality sets of medical image data associated with a same patient; and
　perform a comprehensive analysis of the plurality sets of medical image data to determine a comprehensive diagnosis result associated with the patient.

18. A non-transitory computer-readable medium having a computer program stored thereon, wherein the computer program, when executed by a processor, performs a method for managing medical images, the method comprising:
　receiving medical image data of a plurality of patient cases acquired by at least one image acquisition device;
　determining diagnosis results of the medical image data using an artificial intelligence method;
　determining priority scores for the medical image data based on the respective diagnosis results;
　sorting the medical image data based on the priority scores;
　presenting a queue of the medical image data on a display according to the sorted order; and
　increasing the priority score of the medical image data at a first rate, as a time length since the medical image data enters the queue increases,
　wherein the first rate is reduced to a second rate when the priority score reaches a threshold.

19. The non-transitory computer-readable medium of claim 18, wherein the method further comprises:
　determining an imaging modality and an imaging site used to acquire the medical image data of each patient case, based on image features extracted from the medical image data; and
　selecting, based on the imaging modality and the imaging site, a corresponding image analyzer for analyzing the medical image data of the patient case, to obtain the diagnostic result.

20. The non-transitory computer-readable medium of claim 18, wherein the patient cases are non-emergency cases, and wherein the priority score of the non-emergency cases does not exceed a priority score of an emergency case.

* * * * *